US00PP32682P3

(12) United States Plant Patent
Hofmann

(10) Patent No.: US PP32,682 P3
(45) Date of Patent: Dec. 22, 2020

(54) ***EUPHORBIA* PLANT NAMED 'INCHADIACL'**

(50) Latin Name: *Euphorbia hypericifolia*
Varietal Denomination: INCHADIACL

(71) Applicant: Birgit Hofmann, Rudesheim am Rhein (DE)

(72) Inventor: Birgit Hofmann, Rudesheim am Rhein (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 16/873,452

(22) Filed: Apr. 14, 2020

(65) Prior Publication Data

US 2020/0329603 P1 Oct. 15, 2020

(30) Foreign Application Priority Data

Apr. 15, 2019 (CA) ..... PBR 19-9763

(51) Int. Cl.
*A01H 5/02* (2018.01)
*A01H 6/38* (2018.01)

(52) U.S. Cl.
USPC ..... Plt./302
CPC ..... *A01H 6/385* (2018.05)

(58) Field of Classification Search
USPC ..... Plt./302
CPC ..... A01H 6/385
See application file for complete search history.

*Primary Examiner* — Anne Marie Grunberg
(74) *Attorney, Agent, or Firm* — C. A. Whealy

(57) ABSTRACT

A new and distinct cultivar of *Euphorbia* plant named 'INCHADIACL', characterized by its mounding to semi-trailing plant habit; moderately vigorous growth habit; freely branching habit; freely flowering habit; and inflorescences with multiple white-colored flower bracts.

1 Drawing Sheet

Botanical designation: *Euphorbia hypericifolia.*
Cultivar denomination: 'INCHADIACL'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on Apr. 15, 2019, application number 19-9763. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Euphorbia* plant, botanically known as *Euphorbia hypericifolia* and hereinafter referred to by the name 'INCHADIACL'.

The new *Euphorbia* plant is a product of a planned breeding program conducted by the Inventor in Heidesheim, Germany. The objective of the program is to create and develop new freely branching *Euphorbia* plants with mounding plant habit and multiple white-colored flower bracts per inflorescence.

The new *Euphorbia* plant originated from a cross-pollination by the Inventor in September, 2014 of a proprietary selection of *Euphorbia hypericifolia* identified as code number Ch13-5000-13, not patented, as the female, or seed, parent with a proprietary selection of *Euphorbia hypericifolia* identified as code number Cha13-5020-2, not patented, as the male, or pollen, parent. The new *Euphorbia* plant was discovered and selected by the Inventor as a single flowering plant within the progeny of the stated cross-pollination in a controlled greenhouse environment in Heidesheim, Germany in March, 2017.

Asexual reproduction of the new *Euphorbia* plant by terminal vegetative cuttings in a controlled greenhouse environment in Gensingen, Germany since March, 2017 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'INCHADIACL'. These characteristics in combination distinguish 'INCHADIACL' as a new and distinct *Euphorbia* plant:

1. Mounding to semi-trailing plant habit.
2. Moderately vigorous growth habit.
3. Freely branching habit.
4. Freely flowering habit.
5. Inflorescences with multiple white-colored flower bracts.

Plants of the new *Euphorbia* differ primarily from plants of the female parent selection in the following characteristics:

1. Plants of the new *Euphorbia* are more mounding and denser than and not as upright and open as plants of the female parent selection.
2. Plants of the new *Euphorbia* have broader leaves than plants of the female parent selection.
3. Plants of the new *Euphorbia* have more flower bracts per inflorescence than plants of the female parent selection.
2. Plants of the new *Euphorbia* and the female parent selection differ in flower bract color as plants of the female parent selection have grey-colored flower bracts.

Plants of the new *Euphorbia* differ primarily from plants of the male parent selection in the following characteristics:

1. Plants of the new *Euphorbia* are more mounding and denser than and not as open as plants of the male parent selection.
2. Plants of the new *Euphorbia* flower earlier than plants of the male parent selection.
3. Plants of the new *Euphorbia* have pure white-colored flower bracts whereas plants of the male parent selection have greyish white-colored flower bracts.

Plants of the new *Euphorbia* can be compared to plants of the *Euphorbia hypericifolia* 'Inneuphdia', disclosed in U.S. Plant Pat. No. 17,567. In side-by-side comparisons, plants of the new *Euphorbia* differ primarily from plants of 'Inneuphdia' in inflorescence form as inflorescences of plants of the new *Euphorbia* have more flower bracts than inflorescences of plants of 'Inneuphdia'.

Plants of the new *Euphorbia* can also be compared to plants of the *Euphorbia hypericifolia* 'Ineupdidaz', disclosed in U.S. Plant Pat. No. 26,848. In side-by-side comparisons, plants of the new *Euphorbia* differ primarily from plants of 'Ineupdidaz' in the following characteristics:

1. Plants of the new *Euphorbia* are larger than plants of 'Ineupdidaz'.
2. Plants of the new *Euphorbia* are not as freely branching as plants of 'Ineupdidaz'.

BRIEF DESCRIPTION OF THE PHOTOGRAPHS

The accompanying colored photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

At the top of the photographic sheet is a side perspective view of a typical flowering plant of 'INCHADIACL' grown in a container and at the bottom of the photographic sheet is a close-up view of a typical flowering plant of 'INCHADIACL'.

DETAILED BOTANICAL DESCRIPTION

The aforementioned photographs and following observations and measurements describe plants grown during the spring in 15.25-cm containers in a polyethylene-covered greenhouse in St. Thomas, Ontario, Canada and under cultural practices typical of commercial *Euphorbia* production. During the production of the plants, day temperatures averaged 27° C. and night temperatures averaged 15° C. Plants were eight weeks from planting rooted cuttings when the photographs and description were taken. In the following description, color references are made to The Royal Horticultural Society Colour Chart, 2007 Edition, except where general terms of ordinary dictionary significance are used.

Botanical classification: *Euphorbia hypericifolia* 'INCHADIACL'.

Parentage:

*Female, or seed, parent.*—Proprietary selection of *Euphorbia hypericifolia* identified as code number Ch13-5000-13, not patented.

*Male, or pollen, parent.*—Proprietary selection of *Euphorbia hypericifolia* identified as code number Cha13-5020-2, not patented.

Propagation:

*Type.*—Terminal vegetative cuttings.

*Time to initiate roots, summer.*—About eight to ten days at temperatures about 24° C.

*Time to initiate roots, winter.*—About ten to twelve days at temperatures about 21° C.

*Time to produce a rooted young plant, summer.*—About three weeks at temperatures about 24° C. to 27° C.

*Time to produce a rooted young plant, winter.*—About four weeks at temperatures about 21° C. to 24° C.

*Root description.*—Fine, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Mounding to semi-trailing; inflorescences positioned above and beyond the foliar plane; moderately vigorous growth habit and moderate growth rate.

*Branching habit.*—Freely branching habit; about three primary lateral branches each with about six secondary lateral branches develop per plant.

*Plant height.*—About 24 cm.

*Plant diameter or spread.*—About 39.2 cm.

*Lateral branch description.*—Length: About 22.5 cm. Diameter: About 1.9 mm. Internode length: About 1.9 cm. Aspect: Initially upright to outwardly to eventually semi-trailing. Strength: Strong. Texture and luster: Smooth, glabrous; slightly glossy. Color: Close to 138A; at the nodes, blushed with close to N77D.

*Leaf description.*—Arrangement: Opposite, simple. Length: About 3.2 cm. Width: About 1 cm. Shape: Elliptical. Apex: Broadly acute. Base: Cuneate. Margin: Entire, not lobed. Venation pattern: Pinnate. Texture and luster, upper and lower surfaces: Sparsely to moderately pubescent; matted. Color: Developing leaves, upper surface: Darker than 143A. Developing leaves, lower surface: Close to 138B. Fully developed leaves, upper surface: Close to N137A; venation, close to 138A. Fully developed leaves, lower surface: Close to 138B; venation, close to 137D. Petioles: Length: About 1.3 cm. Diameter:

About 0.6 mm. Strength: Moderately strong. Texture and luster, upper and lower surfaces: Sparsely pubescent; matte. Color, upper and lower surfaces: Close to 144B.

Inflorescence description:

*Inflorescence type and habit.*—Inflorescences are composed of a single cyathia surrounded with about five to ten flower bracts subtending the cyathia; inflorescences positioned above and beyond the foliar plane; freely flowering habit with about one to six inflorescences per node and about 750 to 1,000 inflorescences developing per plant; inflorescences face mostly upright.

*Inflorescence diameter.*—About 1.7 cm.

*Inflorescence height.*—About 7 mm.

*Fragrance.*—None detected.

*Natural flowering season.*—Plants typically flower from the spring until the autumn in southern Ontario, Canada.

*Inflorescence longevity.*—Inflorescences last about four days on the plant; inflorescences not persistent.

*Flower bracts.*—Quantity per inflorescence: About five to ten. Length, largest bracts: About 6.6 mm. Width, largest bracts: About 2.6 mm. Shape: Oblanceolate. Apex: Cuspidate. Base: Attenuate. Margin: Entire, not undulate. Texture and luster, upper surface: Smooth, glabrous; slightly glossy. Texture and luster, lower surface: Smooth, glabrous; matte. Aspect: Mostly horizontal. Venation pattern: Pinnate. Color: Developing and fully expanded bracts, upper surface: Close to NN155D; venation, close to NN155D; color does not change with development. Developing and fully expanded bracts, lower surface: Close to NN155D; venation, close to NN155D; color does not change with development. Flower bract petioles: Length: About 2 mm. Diameter: Less than 1 mm. Texture and luster, upper and lower surfaces: Smooth, glabrous; slightly glossy. Color, upper and lower surfaces: Close to 145C.

*Cyathia.*—Quantity per corymb: One. Diameter: About 2 mm. Height: About 2 mm. Shape: Globose; sessile. Color: Close to 145C. Nectaries: Nectary development has not been observed on plants of the new *Euphorbia.*

*Peduncles.*—Length: About 2.5 mm. Diameter: About 0.8 mm. Strength: Moderately strong. Aspect: About 45° from vertical. Texture and luster: Smooth, glabrous; matte. Color: Close to 137B.

*Reproductive organs.*—Stamens: Stamen development has not been observed on plants of the new *Euphorbia.* Pistils: Quantity per cyathia: One. Pistil length: About 3 mm. Stigma shape: Five-parted. Stigma color: Close to NN155D. Style length: About 1 mm. Style color: Close to 157D. Ovary color: Close to 144B.

*Seeds and fruits.*—To date, seed and fruit production has not been observed on plants of the new *Euphorbia.*

Pathogen & pest resistance: Plants of the new *Euphorbia* have not been shown to be resistant to pathogens and pests common to *Euphorbia* plants.

It is claimed:

1. A new and distinct *Euphorbia* plant named 'INCHADIACL' as illustrated and described.

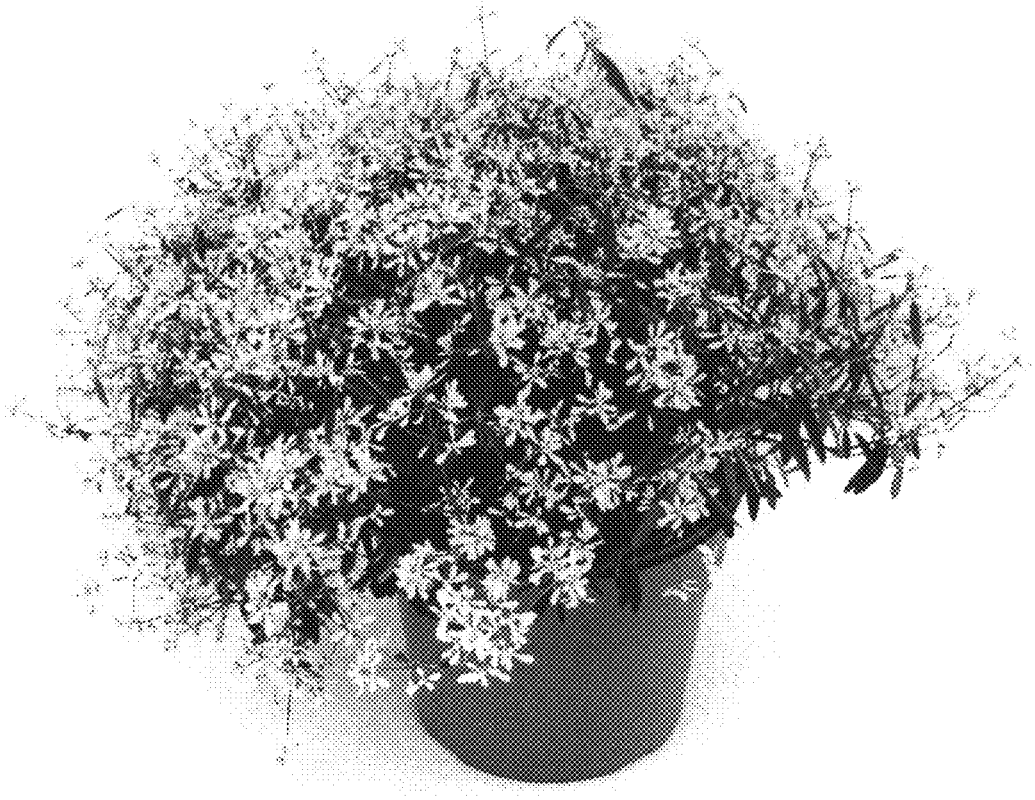
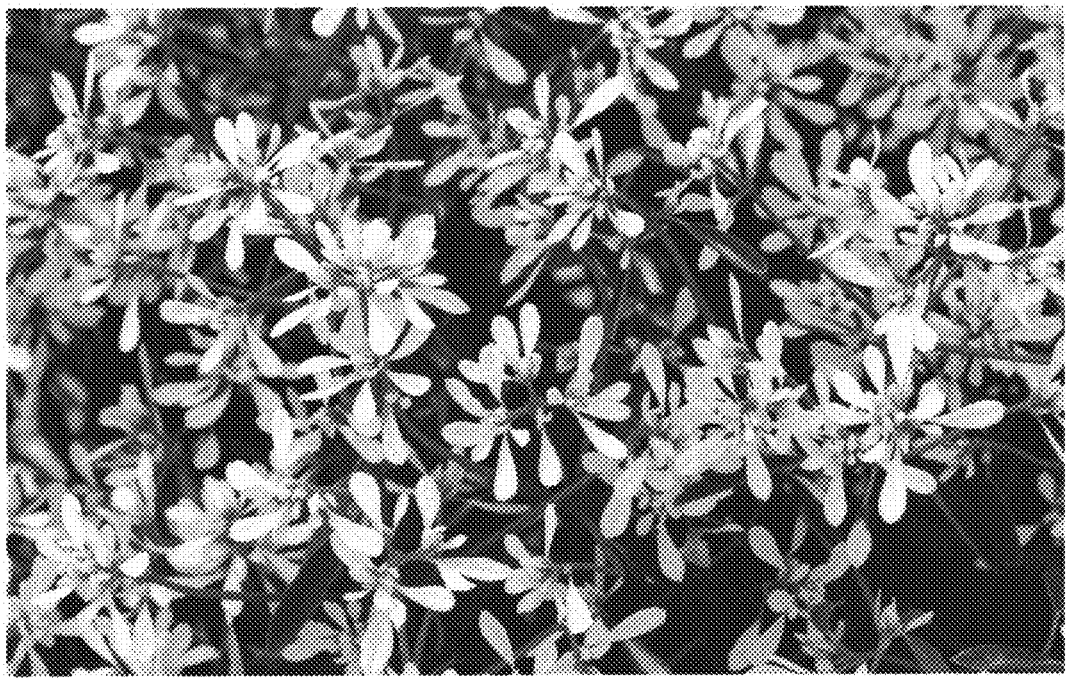

* * * * *